ary—Mark L. Berch

United States Patent [19]
Griffith

[11] Patent Number: 4,517,187
[45] Date of Patent: May 14, 1985

[54] 1,3,4,6,7-11B-HEXAHYDRO-7-PHENYL-2H-PYRAZINO[2,1-A]ISOQUINOLINES METHODS OF PREPARATION, AND USE AS ANTIDEPRESSANTS

[75] Inventor: Ronald C. Griffith, Pittsford, N.Y.

[73] Assignee: Pennwalt Corporation, Philadelphia, Pa.

[21] Appl. No.: 435,132

[22] Filed: Oct. 18, 1982

[51] Int. Cl.³ .................. C07D 487/04; A61K 31/495
[52] U.S. Cl. ..................................... 514/250; 544/344
[58] Field of Search ......................... 544/344; 424/250

[56] References Cited

U.S. PATENT DOCUMENTS

| | | | |
|---|---|---|---|
| 3,393,195 | 7/1968 | Thesing et al. | 544/344 |
| 3,684,813 | 8/1972 | Archer et al. | 544/344 |
| 4,162,319 | 7/1979 | Scubert et al. | 544/344 |

Primary Examiner—Mark L. Berch

[57] ABSTRACT

1,3,4,6,7-11b-Hexahydro-7-aryl-2H-pyrazino[2,1-a]isoquinolines useful as chemical intermediates and as pharmaceuticals and methods for their preparation.

18 Claims, No Drawings

1,3,4,6,7-11B-HEXAHYDRO-7-PHENYL-2H-PYRAZINO[2,1-A]ISOQUINOLINES METHODS OF PREPARATION, AND USE AS ANTIDEPRESSANTS

SUMMARY OF THE INVENTION

The present invention pertains to a new 1,3,4,6,7,11b-hexahydro-7-aryl-2H-pyrazino[2,1-a]isoquinoline of the formula

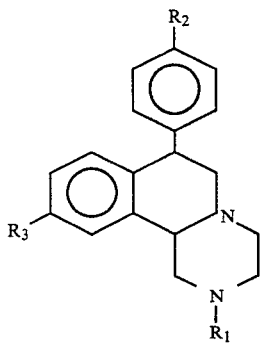

I wherein $R_1$ is hydrogen, lower alkyl, cycloalkyl, alkanoyl, aralkyl, araklanoyl, aryl or aroyl and $R_2$ and $R_3$ are the same or independently hydrogen, halogen, hydroxy, acyloxy, nitro, amino, aminoalkyl, trifluoromethyl, alkyl, alkoxy, acyl, cyano, or alkylamino. By the term "lower alkyl" as used herein is intended an alkyl group, straight or branched, containing about seven or less carbon atoms. This compound and its addition salts both in cis and trans form possesses useful pharmacological properties, particularly antidepressant, antihistaminic and cholinergic activity.

METHODS OF PREPARATION

Methods are well known for the formation of tetrahydro pyrazines from 1,2-ethylene diamines and can be adapted by those skilled in the art of organic chemistry to the conversion of 1,2,3,4-tetrahydro-1-aminomethyl-4-aryl isoquinoline of formula II to the corresponding 1,3,4,6,7,11b-hexahydro-7-aryl-2H-pyrazino-[2,1-a]isoquinolines of formula I. A particularly useful method for accomplishing this is that of Riebsomer [J. L. Riebsomer, *J. Org. Chem.*, 15, 68 (1950)], which utilizes oxalic acid or its esters to form the two carbon bridge between the amine functions of ethylene diamine derivatives. Other two carbon synthons can be utilized, for example ethylene dibromide, ethylene glycol, 2-haloethanols and ethylene oxide.

The preferred embodiment for producing compounds of formula I comprises reacting the compound of formula II

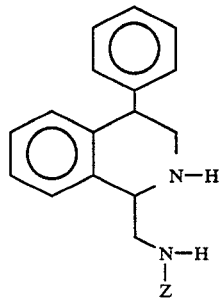

II (wherein Z is hydrogen or lower alkyl) with oxalic acid or its functional derivatives, especially its lower alkyl esters, such as the dimethyl or diethyl ester of oxalic acid to give the compound of formula III.

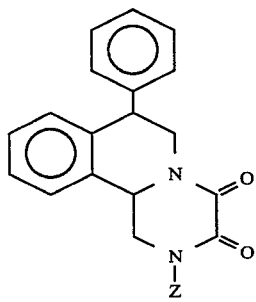

III

This reaction can be accomplished in the absence of a solvent or with an inert solvent such as toluene or chloroform. A further embodiment of this process when the salts of formula II, for example the dihydrochloride, are used, the addition of equimolar quantities of a base such as triethylamine or pyridine to the reaction liberates the base in situ and allows the reaction to proceed.

When oxalate esters are used, elevated temperatures of about 50° C. to 120° C. are required for completion of the reaction, although lower or higher temperatures can be used. By further reacting the compound of formula III with complex hydride reducing agents such as borane, borane methylsulfide or lithium aluminum hydride in solvents such as ether, tetrahydrofuran or dioxane, the compound of formula I is obtained.

Alternatively, the compound of formula II can be reacted with an ethylene moiety X-CH$_2$-CH$_2$-Y, where X and Y are the same or independently halogen or hydroxyl or together form ethylene oxide and in the case where X or Y is halogen, preferably both bromine, it is advantageous to add a base such as pyridine or triethylamine. The compound of formula I is thus formed directly and the reduction step is eliminated.

In a further process modification, advantageous for preparing compounds of formula I where $R_1$ is other than hydrogen, the compound of formula I where $R_1$ is hydrogen is first prepared either (i) from the compound of formula II where Z is hydrogen, or (ii) by dealkylation of the compound of formula I where $R_1$ is lower alkyl. The dealkylation is accomplished by reacting the alkylated derivative with a dealkylating agent such as methylchlorformate or cyanogen bromide to remove the N-lower alkyl substituent. In using the preferred reagent for dealkylation, methyl chloroformate, the reaction is carried out in an inert solvent such as chloroform, in the presence of a base such as sodium carbonate, at elevated temperatures for a period from about 2 hours to 48 hours. The urethane derivative thus obtained is then hydrolyzed with a base, for example hydrazine, to produce the compound of formula I where $R_1$ is hydrogen.

The formula I compound where $R_1$ is other than hydrogen is prepared by reacting the dealkylated compound with an acyl halide or an equivalent reagent RCOX to obtain the amide derivative of formula IV.

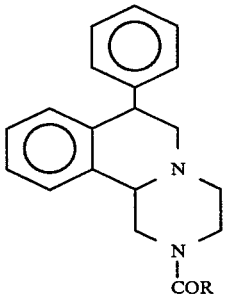

IV where the RCO group on reduction with a complex hydride reagent produces the compound of formula I. The R of RCOX is therefore defined as hydrogen, lower alkyl, cycloalkyl, aryl or aralkyl.

The complex hydrides are, for example borane, borane methylsulfide or lithium aluminum hydride and the reactions are carried out in solvents such as tetrahydrofuran, ether or dioxane at temperatures from about 0° C. to 120° C.

In addition to the processes already described, aromatic substituted derivatives of I, that is derivatives where $R_2$ and/or $R_3$ are other than hydrogen, may also be prepared by direct electrophilic aromatic substitution of corresponding unsubstituted compounds of formula I. Thus compounds of formula I wherein $R_2$ and/or $R_3$ are hydrogen can be reacted with electrophilic reagents, e.g., nitric acid or acylating reagents in the presence of acids, i.e., sulfuric, trifluoroacetic, aluminum chloride or stannic chloride, to produce aromatic ring substituted formula I embodiments.

Particularly useful aromatic ring substituted embodiments are those where $R_2$ and/or $R_3$ are nitro. The nitro derivative can be reduced to the corresponding amines and the corresponding aryl diazonium salts can be prepared according to conventional methods, to provide further derivatives where $R_2$ and/or $R_3$ are halogen (i.e., fluorine, bromine, chlorine, iodo), hydroxy, amino, alkylamino, cyano and alkoxy.

Illustrative techniques and processes for the preparation of the compounds of formula I are presented in the following specific non-limiting Examples. Temperatures are in degrees centigrade unless otherwise indicated.

The antihistaminic activity as reported in the Examples was determined by in vitro inhibition of histamine-stimulated . adenylate cyclase (ad. cyc H) by the method developed by Kanof and Greengard, (Nature, 272, p. 329, 1978), or by in vitro inhibition of the specific binding of tritiated mepyramine ([$^3$H]-mepyramine) in brain as described by Tran, et al., (Proc. Nat'l. Acad. Sci. USA, 75 p. 6290, 1978). Cholinergic activity was determined by in vitro inhibition of the binding of tritiated quinuclidinyl benzylate ([$^3$H]-QNB) in brain as described by Yamamura and Snyder, (Proc. Nat'l. Acad. Sci. USA, 71 p.1725, 1974). Antidepressant activity was determined in vitro by comparing the measured cholinergic and antihistaminic activities as described above with that of standard tricyclic antidepressant drugs such as imipramine, amitriptyline and doxepin, as well as the atypical antidepressant standards mianserin and iprindole. Further, antidepressant activity was determined in vivo by computer analysis of the EEG's of conscious beagles by the method described by Frankenheim, J., et al., (Pharmacologist 22, p. 298, 1980). These observations are reported in various Examples which follow in terms of "potency" where potency is expressed as the molar concentration required to inhibit by 50% the stimulation of adenylate cyclase observed after treatement with histamine (ad cyc H), or the binding of [$^3$H]mepyramine or [$^3$H]QNB to rate brain homogenates. The smaller numbers indicate greater potency.

EXAMPLE 1

Synthesis of cis-1,3,4,6,7,11b-Hexahydro-2-methyl-7-phenyl-2H-pyrazino[2,1-a]isoquinoline dihydrochloride N-Chloroacetyl-2,2-diphenylethylamine To a stirred solution of 2,2-diphenylethylamine (100.0 g, 0.5 m) and triethylamine (123.0 g, 1.2 m) in chloroform (2 liters) maintained under nitrogen at ambient temperature was added dropwise chloroacetylchloride (124.2 g, 1.1 m) and the mixture stirred for 2 hours. Thin layer chromatography (TLC) analysis showed the reaction to be complete. The mixture was transferred to a separatory funnel and washed with 10% HCl (3 ×1 liter) and water (1 liter) and the organic phase dried over MgSO$_4$. The solvent was evaporated to a dark oil which was treated with cyclohexane (1 liter) and, upon standing, a solid crystallized which was collected by filtration, washed with cyclohexane and air dried to give 122.0 g of N-chloroacetyl-1,1-diphenylethylamine as a tan solid, m.p. 73°–74°.

1-Chloromethyl-3,4-dihydro-4-phenylisoquinoline hydrochloride

A stirred suspension of phosphorus pentoxide (373.0 g, 2.6 m) in xylene (8 liters) maintained under nitrogen was heated to a gentle reflux (ca 140° ) and then treated portionwise with N-chloroacetyl-1,1-diphenylethylamine (90.0 g, 0.328 m) and the mixture maintained at reflux for 2 hours, then allowed to cool to ambient temperature overnight. The xylene was decanted off, the reaction flask was cooled in an ice bath, and the solid residue carefully treated with water (10 liters). This mixture was stirred for 0.5 hour, then basified to pH 11 with 50% NaOH, and extracted with chloroform (3×3 liters) and the extracts dried over MgSO$_4$. The solvents were evaporated to a dark oil which was immediately dissolved in a mixture of acetone (500 ml) and ether (200 ml) and acidified with HCl gas. Upon standing, a solid crystallized which was collected by filtration and air dried to give 88.1 g of 1-chloromethyl-3,4-dihydro-4-phenyl-isoquinoline hydrochloride, m.p. 206°–207°.

Cis and trans-1,2,3,4-tetrahydro-1-methylaminomethyl-4-phenylisoquinoline dihydrochloride To a stirred solution of methanol (1 liter) and monomethylamine (300 ml) maintained under nitrogen and cooled in an ice bath was added portionwise 1-chloromethyl-3,4-dihydro-4-phenylisoquinoline hydrochloride (83.0 g, 0.28 m) and the mixture heated to reflux (ca 50°-55°) for 2 hours. After cooling, the solution was poured into a pressure bottle and hydrogenated on a Parr apparatus over 5% Pd/C catalyst (5.0 g) at 40 psi for 16 hours. The catalyst was removed by filtration and the solvent evaporated to a gummy residue. This was dissolved in a mixture of methanol (200 ml) and isopropanol (200 ml) and acidified with HCl gas. Upon cooling and standing, a white solid crystallized which was collected by filtration and dried to give 64.0 g of the major isomer cis-1,2,3,4-tetrahydro-1-methylaminomethyl-4-phenyl-isoquinoline dihydrochloride, m.p. 276°-277°. A second crop of solid was obtained from the crystallization (26.1 g) which consisted (TLC) mostly of the minor isomer. Two recrystallizations of this crop provide the pure minor isomer trans-1,2,3,4-tetrahydro-1-methylaminomethyl-4-phenylisoquinoline, m.p. 269°-270°.

Cis-1,3,4,6,7,11b-Hexahydro-2-methyl-7phenyl-2H-pyrazino[2,1-a]isoquinoline-3,4-dione To a stirred solution of cis-1,2,3,4-tetrahydro-1-methylaminomethyl-4-phenylisoquinoline dihydrochloride (30.6 g, 0.094 m) in chloroform (500 ml) maintained under nitrogen at ambient temperature was added triethylamine (42.6 g, 0.42 m) and then in one portion diethyloxalate (30.1 g, 0.206 m) and the mixture heated to reflux for 4 hours. The mixture was cooled and washed with 10% HCl (3×150 ml) and water (150 ml), then dried over MgSO$_4$. The solvent was evaporated to give 22.3 g of cis-1,3,4,6,7,11b-hexahydro-2-methyl-7-phenyl-2H-pyrazino[2,1-a]isoquinoline-3,4-dione as a pale yellow solid. An analytical sample, recrystallized from isopropanol, had m.p. 193°-194°.

Cis-1,3,4,6,7,11b-Hexahydro-2-methyl-7-phenyl-2H-pyrazino[2,1-a]isoquinoline dihydrochloride To a stirred solution of 1.0 M borane in tetrahydrofuran (450 ml) maintained under nitrogen at ambient temperature was added a solution of cis-1,3,4,6,7,11b-hexahydro-2-methyl-7-phenyl-2H-pyrazino[2,1-a]isoquinoline-3,4-dione (22.3 g, 0.0728 m) in tetrahydrofuran (100 ml), refluxed for 1 hour and the solvent removed on an aspirator, leaving a solid residue. This was treated with water (250 ml), basified to pH 11 with 50% NaOH and extracted with chloroform (3×250 ml). The chloroform extracts were dried over MgSO$_4$ and evaporated to a pale yellow oil. This was dissolved in methanol (200 ml) and isopropanol (100 ml) and acidified with HCl gas. Upon standing, a white solid crystallized which was collected by filtration, washed with isopropanol/ether, and vacuum dried to give 18.1 g of cis-1,3,4,6,7,11b-hexahydro-2-methyl-7-phenyl-2H pyrazino[2,1-a]-isoquinoline dihydrochloride, m.p. 272°-273°. The product has an ad cyc H rating of 6.8×10$^{-6}$ M, a ($^3$H)mepyramine rating of 2.0×10$^{-8}$ M and a ($^3$H)QNB of 2.5×10$^{-7}$ M.

EXAMPLE 2

Synthesis of trans-1,3,4,6,7,11b-Hexahydro-2-methyl-7-phenyl-2H-pyrazino[2,1-a]isoquinoline dihydrochloride

Trans-1,3,4,6,7,11b-Hexahydro-2-methyl-7-phenyl-2H-pyrazino[2,1-a]isoquinoline-3,4-dione Using the techniques described in Example 1, 4.8 g of trans-1,2,3,4-tetrahydro-1-methylaminomethyl-4-phenylisoquinoline dihydrochloride is reacted with 4.5 g ethyloxalate in the presence of triethylamine to provide 4.2 g of trans-1,3,4,6,7,11b-hexahydro-2-methyl-7-phenyl- 2H-pyrazino[2,1-a]isoquinoline-3,4-dione.

Trans-1,3,4,6,7,11b-Hexahydro-2-methyl-7-phenyl-2H-pyrazino[2,1-a]isoquinoline dihydrochloride Using the procedure as described in Example 1 hereinabove, 4.2 g of trans-1,3,4,6,7,11b-hexahydro-2-methyl-7-phenyl-2H-pyrazino[2,1-a]isoquinoline-3,4-dione was reduced with 150 ml of 1.0 M borane in tetrahydrofuran to produce, after salt formation, recrystallization and drying, 1.0 g of trans-1,3,4,6,7,11b-hexahydro-2-methyl-7-phenyl-2H-pyrazino[2,1-a]isoquinoline dihydrochloride, m.p. 279°-280°. The product has an ad cyc H rating greater than 1×10$^{-5}$ M, a ($^3$H)mepyramine rating greater than 1×10$^{-6}$ M and a ($^3$H)QNB rating of 3.3×10$^{-6}$ M.

EXAMPLE 3

Synthesis of cis-1,3,4,6,7,11b-Hexahydro-2-ethyl-7-phenyl-2H-pyrazino[2,1-a]isoquinoline dihydrochloride

Cis-1,3,4,6,7,11b-Hexahydro-2-ethyl-7-phenyl-2H-pyrazino2,1-a]isoquinoline-3,4-dione To a stirred solution of cis-1,2,3,4-tetrahydro-1-(ethylamino)methyl-4-phenyl-isoquinoline dihydrochloride (19.5 g, 0.057 m) in chloroform (250 ml) maintained under nitrogen at ambient temperature was added triethylamine (26.0 g, 0.25 m) and then in one portion diethyl oxalate (36.4 g, 0.23 m) and the mixture heated to reflux for 5 hours. The mixture was cooled and washed with 10% HCl (3×150 ml) and water (200 ml) and dried over MgSO$_4$. The solvent was evaporated to a yellow oil, which was dissolved in 200 ml ethanol, decolorized with Norite. Upon cooling and standing, a white solid crystallized which was collected by filtration and dried to give 11.2 g of cis-1,3,4,6,7,11b-hexahydro-2-ethyl-7-phenyl-2H-pyrazino[2,1-a]isoquinoline-3,4-dione.

Cis-1,3,4,6,7,11b-Hexahydro-2-ethyl-7-phenyl-2H-pyrazino[2,1-a]isoquinoline dihydrochloride To a stirred solution of 1.0 M borane in tetrahydrofuran (200 ml) maintained under nitrogen at ambient temperature was added cis-1,3,4,6,7,11b-hexahydro-2-ethyl-7-phenyl-2H-pyrazino[2,1-a]isoquinoline-3,4-dione (9.9 g, 0.03 m) and the mixture heated to reflux for 2 hours. The mixture was cooled in an ice bath and carefully treated with 10% HCl (125 ml), refluxed for 1 hour, and the solvent removed on an aspirator. The residue was treated with water (300 ml), basified to pH 11 with 50% NaOH, and extracted with chloroform. The extracts were dried over MgSO$_4$ and evaporated to a pale yellow oil. This oil was dissolved in methanol (100 ml) and isopropanol (100 ml) and acidified with HCl gas. Upon cooling and standing, a white solid crystallized which was collected by filtration. Recrystallization and vacuum drying gave 4.0 g of cis-1,3,4,6,7,11b-hexahydro-2-ethyl-7-phenyl-2H-pyrazino[2,1-a]isoquinoline dihydrochloride, m.p. 276°–277° C. The product has an ad cyc H rating greater than $1 \times 10^{-5}$ M, a ($^3$H)mepyramine rating of $3.4 \times 10^{-7}$ and a ($^3$H)QNB rating of $1.1 \times 10^{-6}$ M.

EXAMPLE 4

Synthesis of cis-1,3,4,6,7,11b-Hexahydro-7-phenyl-2H-pyrazino[2,1-a]isoquinoline dihydrochloride To a stirred solution of cis-1,3,4,6,7,11b-hexahydro-2-methyl-7-phenyl-2H-pyrazino[2,1-a]isoquinoline (11.0 g, 0.039 m) in chloroform (1500 ml) was added sodium bicarbanate (83.1 g, 0.99 m) and methyl chloroformate (45.3 g, 0.48 m), and the mixture heated to reflux for 48 hours. The salts were removed by filtration and the organic phase washed with 5% HCl ($3 \times 300$ ml) and water (300 ml) and dried over MgSO$_4$. The solvent was evaporated and the oily residue treated with 95% hydrazine (250 ml) and refluxed for 24 hours. Water (500 ml) was added and the mixture evaporated to an oily residue. This was treated with water (500 ml) and a small amount of 50% NaOH to ensure pH 11, and the mixture extracted with chloroform ($3 \times 250$ ml). The extracts were dried over MgSO$_4$ and evaporated to a yellow oil. This was dissolved in methanol (50 ml) and isopropanol (50 ml) and acidified with HCl gas. Upon standing and cooling, a white solid crystallized, which was collected by filtration. Recrystallization from methanol/isopropanol/water and vacuum drying gave 6.4 g of cis-1,3,4,6,7,11b-hexahydro-7-phenyl-2H-pyrazino[2,1-a]isoquinoline dihydrochloride, m.p. 275°–277°. The product has an ad cyc H rating greater than $1 \times 10^{-5}$ M, a ($^3$H)mepyramine rating greater than $1 \times 10^{-6}$ M and a ($^3$H)QNB of $9.2 \times 10^{-7}$ M.

EXAMPLE 5

Synthesis of cis-1,3,4,6,7,11b-Hexahydro-7-phenyl-2-propyl-2H-pyrazino[2,1-a]isoquinoline dihydrochloride Cis-1,3,4,6,7,11b-Hexahydro-7-phenyl-2-propionyl-2H-pyrazino[2,1-a]isoquinoline To a stirred solution is cis-1,3,4,6,7,11b-hexahydro-7-phenyl-2H-pyrazino[2,1-a]isoquinoline dihydrochloride (7.0 g, 0.20 m) and triethylamine (8.4 g, 0.08 m) in chloroform (100 ml) maintained at 0° under nitrogen was added dropwise propionyl chloride (2.9 g, 0.031 m). The mixture was allowed to warm to ambient temperature and stirred for 16 hours, then treated with 10% HCl (50 ml). The layers were separated and the organic phase washed with 10% HCl ($2 \times 50$ ml), water (50 ml), and dried over MgSO$_4$. Evaporation of the solvent gave a solid residue, which was slurred with ether and filtered to give 2.1 g cis-1,3,4,6,7,11b-hexahydro-7-phenyl-2-propionyl-2H-pyrazino[2,1-a]isoquinoline, m.p. 250°–251°. An additional 3.2 g of good purity product was recovered from the ether to give a total of 5.3 g (82%).

Cis-1,3,4,6,7,11b-Hexahydro-7-phenyl-2-propyl-2H-pyrazino[2,1-a]isoquinoline dihydrochloride To a stirred solution of 1.0 M borane in tetrahydrofuran (55 ml) maintained under nitrogen at 0° C. was added cis-1,3,4,6,7,11b-hexahydro-7-phenyl-2-propionyl-2H-pyrazino[2,1-a]isoquinoline (5.3 g, 0.016 m) and the mixture heated to reflux for 3 hours, then cooled in an ice bath and carefully treated with 10% HCl (100 ml). This mixture was heated to reflux for 1 hour, then cooled, and the tetrahydrofuran removed on an aspirator. The remaining aqueous solution was basified to pH 11 with 50% NaOH and extracted with chloroform. The extracts were dried over MgSO$_4$ and evaporated to a solid residue (6.0 g). This was dissolved in methanol (50 ml) and isopropanol (50 ml) and acidified with HCl gas. Upon cooling and standing, a white solid crystallized, which was collected by filtration and vacuum dried at 80° for 24 hours to give 4.6 g cis-1,3,4,6,7,11b-hexahydro-7-phenyl-2-propyl-2H-pyrazino[2,1-a]isoquinoline dihydrochloride, m.p. 273°–274°.

EXAMPLE 6

Synthesis of cis-1,3,4,6,7,11b-Hexahydro-2-butyl-7-phenyl-2H-pyrazino[2,1-a]isoquinoline dihydrochloride Cis-1,3,4,6,7,11b-Hexahydro-2-butyryl-7-phenyl-2H-pyrazino[2,1-a]isoquinoline To a stirred solution of cis-1,3,4,6,7,11b-hexahydro-7-phenyl-2H-pyrazino[2,1-a]isoquinoline dihydrochloride (7.8 g, 0.023 m) and triethylamine (9.4 g, 0.93 m) in chloroform (100 ml) maintained at 0° under nitrogen was added dropwise butyryl chloride (3.8 g, 0.0356 m). The mixture was allowed to warm to ambient temperature and stirred for 3 hours, then treated with 10% HCl (50 ml). The layers were separated and the organic phase washed with 10% HCl ($2 \times 50$ ml), water (50 ml), and dried over MgSO$_4$. Evaporation of the solvent gave an oily residue which was dissolved in tetrahydrofuran (100 ml) and a white solid crystallized which was collected by filtration to give 5.1 g of cis-1,3,4,6,7,11b-hexahydro-2-butyryl-7-phenyl-2H-pyrazino[2,1-a]isoquinoline, m.p. 212°–213°. An additional 3.5 of good purity product was recovered from the tetrahydrofuran to give a total of 8.6 g (93%).

Cis-1,3,4,6,7,11b-Hexahydro-2-butyl-7-phenyl-2H-pyrazino[2,1-a]isoquinoline dihydrochloride To a stirred solution of 1.0 M borane in tetrahydrofuran (100 ml) maintained under nitrogen at ambient temperature was added cis-1,3,4,6,7,11b-hexahydro-2-butyryl-7-phenyl-2H-pyrazino[2,1-a]isoquinoline (8.6 g, 0.021 m) and and the mixtdre heated to reflux for 3 hours, then cooled in an ice bath and carefully treated with 20% HCl (100 ml). This mixture was heated to reflux for 1 hour, then cooled, and the tetrahydrofuran removed on an aspirator. The remaining aqueous solution was basified to pH 11 with 50% NaOH and extracted with chloroform ($3 \times 50$ ml). The extracts were dried over MgSO$_4$ and evaporated to an oily residue. This was dissolved in methanol (50 ml) and isopropanol (50 ml) and acidified with HCl gas. The white solid, which precipitated immediately, was collected by filtration, recrystallized from methanol/ether, and vacuum dried at 90° for 24 hours to give 5.7 g of cis-1,3,4,6,7,11b-hexahydro-2-butyl-7-phenyl-2H-pyrazino[2,1-a]isoquinoline dihydrochloride, m.p. 261°–262°.

EXAMPLE 7

Synthesis of cis-1,3,4,6,7,11b-Hexahydro-2-hexyl-7-phenyl-2H-pyrazino[2,1-a]isoquinoline dihydrochloride Cis-1,3,4,6,7,11b-Hexahydro-2-hexanoyl-7-phenyl-2H-pyrazino[2,1-a]isoquinoline To a stirred solution of cis-1,3,4,6,7,11b-hexahydro-7-phenyl-2H-pyrazino[2,1-a]isoquinoline dihydrochloride (7.8 g, 0.023 m) and triethylamine (9.4 g, 0.093 m) in chloroform (100 ml) maintained at 0° under nitrogen was added dropwise hexanoyl chloride (4.79 g, 0.0356 m). The mixture was allowed to warm to ambient temperature and stirred for 3 hours, then treated with 10% HCl (25 ml). The layers were separated and the organic phase washed with 10% HCl (2×25 ml), water and dried over MgSO₄. Evaporation of the solvent gave an oily residue which was dissolved in tetrahydrofuran and a white solid crystallized which was collected by filtration to give 6.4 g of cis-1,3,4,6,7,11b-hexahydro-2-hexanoyl-7-phenyl-2H-pyrazino[2,1-a]isoquinoline, m.p. 163°–164.5°. An additional 3.1 g of good purity product was recovered from the tetrahydrofuran to give a total of 9.5 g.

Cis-1,3,4,6,7,11b-Hexahydro-2-hexyl-7-phenyl-2H-pyrazino[2,1-a]isoquinoline dihydrochloride To a stirred solution of 1.0 M borane in tetrahydrofuran (100 ml) maintained under nitrogen at ambient temperature was added cis-1,3,4,6,7,11b-hexahydro-2-hexanoyl-7-phenyl-2H-pyrazino[2,1-a]isoquinoline (8.3 g, 0.019 m) and the mixture heated to reflux for 3 hours, then cooled in an ice bath and carefully treated with 10% HCl (100 ml). This mixture was heated to reflux for 1 hour, then cooled, and the tetrahydrofuran removed on an aspirator. The residue was treated with 20% NaOH (300 ml) and extracted with chloroform (3×75 ml). The extracts were dried over MgSO₄ and evaporated to an oily residue, 12.3 g. This was dissolved in methanol (100 ml) and isopropanol (50 ml) and acidified with HCl gas. A white solid crystallized which was collected by filtration, recrystallized from methanol/water, and vacuum dried at 110° for 24 hours to give 7.1 g cis-1,3,4,6,7,11b-hexahydro-2-hexyl-7-phenyl-2H-pyrazino[2,1-a]isoquinoline dihydrochloride, m.p. 221°–222°.

EXAMPLE 8

Synthesis of cis-1,3,4,6,7,11b-Hexahydro-2-benzyl-7-phenyl-2H-pyrazino[2,1-a]pyrazino[2,1-a]isoquinoline dihydrochloride Cis-1,3,4,6,7,11b-Hexahydro-2-benzoyl-7-phenyl-2H-pyrazino[2,1-a]isoquinoline To a stirred solution of cis-1,3,4,6,7,11b-hexahydro-7-phenyl-2H-pyrazino[2,1-a]isoquinoline dihydrochloride (9.2 g, 0.027 m) and triethylamine (10.9 g, 0.108 m) in chloroform (125 ml) maintained at 0° under nitrogen was added benzoyl chloride (5.8 g, 0.041 m). The mixture was allowed to warm to ambient temperature and stirred for 3 hours, then treated with 10% HCl (50 ml). The layers were separated, and the organic phase was washed with 10% HCl (2×50 ml), water and then dried over MgSO₄. Evaporation of the solvent gave an oily residue (9.2 g), which was treated with ether (100 ml), and the resulting white solid precipitate collected by filtration to give 6.8 g of cis-1,3,4,6,7,11b-hexahydro-2-benzoyl-7-phenyl-2H-pyrazino[2,1-a]isoquinoline, m.p. 279°–280°.

Cis-1,3,4,6,7,11b-Hexahydro-2-benzyl-7-phenyl-2H-pyrazino[2,1-a]isoquinoline dihydrochloride To a stirred solution of 1.0 M borane in tetrahydrofuran (70 ml) maintained under nitrogen at 0° was added cis-1,3,4,6,7,11b-hexahydro-2-benzoyl-7-phenyl-2H-pyrazino[2,1-a]isoquinoline (6.8 g, 0.0184 m) and the mixture heated to reflux for 3 hours, then cooled in an ice bath and carefully treated with 10% HCl (50 ml). This mixture was heated to reflux for 1 hour, then cooled, and tetrahydrofuran removed on an aspirator. The residue was basified to pH 11 with 10% NaOH and extracted with chloroform (3×100 ml). The extracts were dried over MgSO₄ and evaporated to a yellow oil, 7.8 g. This crude product was purified by chromatography on a Prep 500 HPLC on silica gel eluting with 1:1 ether:cyclohexane (1% diethylamine). The pure fractions were combined and evaporated to an oil which was dissolved in methanol (50 ml) and isopropanol (25 ml) and acidified with HCl gas. The white solid which crystallized was collected by filtration and vacuum dried at 80° for 24 hours to give 3.9 g of cis-1,3,4,6,7,11b-hexahydro-2-benzyl-7-phenyl-2H-pyrazino[2,1-a]isoquinoline dihydrochloride, m.p. 203°–204°.

EXAMPLE 9

Synthesis of cis-1,3,4,6,7,11b-Hexahydro-2-phenethyl-7-phenyl-2H-pyrazino2,1-a]isoquinoline dihydrochloride Cis-1,3,4,6,7,11b-Hexahydro-2-phenylacetyl-7-phenyl-2H-pyrazino[2.1-a]isoquinoline To a stirred solution of cis-1,3,4,6,7,11b-hexahydro-7-phenyl-2H-pyrazino[2,1-a]isoquinoline dihydrochloride (7.8 g, 0.023 m) and triethylamine (9.4 g, 0.093 m) in chloroform (100 ml) maintained at 0° under nitrogen was added phenylacetyl chloride (5.6 g, 0.0356 m). The mixture was allowed to warm to ambient temperature and stirred for 3 hours, then treated with 10% HCl (100 ml). The layers were separated and the organic phase washed with 10% HCl (3×100 ml), water and dried over MgSO₄. Evaporation of the solvent gave an oily residue (12.0 g), which was treated with tetrahydrofuran (50 ml), and the resulting white solid precipitate collected by filtration and air dried to give 6.2 g of cis-1,3,4,6,7,11b-hexahydro-2-phenylacetyl-7-phenyl-2H-pyrazino[2,1-a]isoquinoline, m.p. 169°–170°.

Cis-1,3,4,6,7,11b-Hexahydro-2-phenethyl-7-phenyl-2H-pyrazino[2,1-a]isoquinoline dihydrochloride To a stirred solution of 1.0 M borane in tetrahydrofuran (100 ml) maintained under nitrogen at ambient temperature was added cis-1,3,4,6,7,11b-hexahydro-2-phenylacetyl-7-phenyl-2H-pyrazino[2,1-a]isoquinoline (6.2 g, 0.016 m) and the mixture heated to reflux for 3 hours, then cooled in an ice bath and carefully treated with 10% HCl (100 ml). This mixture was heated to reflux for 1 hour, then cooled, and the tetrahydrofuran removed on an aspirator. The remaining aqueous residue was basified to pH 11 with 50% NaOH and extracted with chloroform (3×75 ml). The extracts were dried over MgSO₄ and evaporated to an oily residue. This was dissolved in methanol (50 ml) and isopropanol (50 ml) and acidified with HCl gas. A white solid crystallized, which was collected by filtration (8.6 g). This solid was recrystallized from methanol (100 ml) and water (1 ml) to give, after vacuum drying at 90° for 24 hours, 3.9 g of cis-1,3,4,6,7,11b-hexahydro-2-phenethyl-7-phenyl-2H-pyrazino[2,1-a]isoquinoline dihydrochloride, m.p. 265°–266°.

Since the compound of this invention contains asymmetric centers, optical isomers are also possible. Thus, we are able by either asymmetric synthesis or optical resolution to obtain the separate optical isomers. The following two examples (10 and 11), describe the optical resolution of the compound of formula I where $R_1$ is $CH_3$ and $R_2$ and $R_3$ are both H and the preparation of the (+) and (−) optical antipodes.

EXAMPLE 10

Optical Resolution of (±)-cis-1,2,3,4,6,7,11b-Hexahydro-2-methyl-7-phenyl-2H-pyrazino[2,1-a]isoquinoline. Preparation of (-)-cis-1,3,4,6,7,11b-Hexahydro-2-methyl-7-phenyl-2H-pyrazino[2,1-a]isoquinoline dihydrochloride (−)-Cis-1,3,4,6,7,11b-Hexahydro-2-methyl-7-phenyl-2H-pyrazino[b 2,1-a]isoquinoline (−)-dibenzoyl-L-tartrate (2:1)

A stirred solution of (±)- cis-1,3,4,6,7,11b-hexahydro-2-methyl-7-phenyl-2H-pyrazino[2,1-a]isoquinoline (21.8 g, 0.0784 m) in 95% ethanol (300 ml) was heated to reflux and then treated with a solution of (−)-dibenzoyl-L-tartaric acid monohydrate (14.32 g, 0.04 m) in hot 95% ethanol (100 ml). A white solid crystallized immediately. The suspension was stirred and refluxed for 15 minutes, then allowed to cool to ambient temperature and the solid collected by filtration and dried to give 17.51 g of salt $[\alpha]^{20} = -135.5°$ (C=0.2, $CH_3OH$). This solid was resuspended in 95% ethanol, stirred and heated to reflux for 1 hour, then allowed to cool and the white solid collected by filtration and vacuum dried to give 16.95 g of fully resolved (−)-cis-1,3,4,6,7,11b-hexahydro-2-methyl-7-phenyl-2H-pyrazino[2,1-a]isoquinoline. (−)-dibenzoyl-L-tartrate (2:1), m.p. 203°–204° dec, $[\alpha]^{20} = -136°$ (C=0.2, $CH_3OH$).

(−)-Cis-1,3,4,6,7,11b-Hexahydro-2-methyl-7-phenyl-2H-pyrazino[2,1-a]isoquinoline dihydrochloride (−)- Cis-1,3,4,6,7,11b-hexahydro-2-methyl-7-phenyl-2H-pyrazino[2,1-a]isoquinoline . (−)-dibenzoyl-L-tartrate (2:1) (16.9 g, 0.01886 m) was dissolved in chloroform (300 ml) and treated with water (600 ml), then basified to pH 11 with 28% aqueous ammonia. The layers were shaken vigorously and separated, and the aqueous phase extracted with chloroform (2×250 ml). The combined chloroform extracts were washed with water (2×100 ml) and dried over $MgSO_4$. Evaporation of the solvent gave 10.1 g (96% yield) of the white solid base. This was dissolved in methanol (200 ml), hot filtered, and the solution acidified with HCl gas. The white solid salt crystallized rapidly. The mixture was stirred and heated to reflux for 10 minutes, then allowed to cool. The solid was collected by filtration, washed with methanol, and vacuum dried at 85° for 24 hours to give 12.7 g of (−)- cis-1,3,4,6,7,11b-hexahydro-2-methyl-7-phenyl-2H-pyrazino[2,1-a]isoquinoline dihydrochloride, m.p. 274°–276° dec, $[\alpha9^{20} = -80.5°$ (C=1, 95% ethanol).

EXAMPLE 11

Optical Resolution of (±)-cis-1,3,4,6,7,11b-hexahydro-2-methyl-7-phenyl-2H-pyrazino[2,1-a]isoquinoline. Preparation of (+)-cis-1,3,4,6,7,11b-Hexahydro-2-methyl-7-phenyl-2H-pyrazino[2,1-a]isoquinoline dihydrochloride (+)-Cis-1,3,4,6,7,11b-Hexahydro-2-methyl-7-phenyl-2H-pyrazino[2,1-a]isoquinoline (+)-dibenzoyl-D-tartrate (2:1)

The first filtrate from Example 10 (preparation of the (−)-dibenzoyl-L-tartrate salt) was evaporated to dryness to a foamy residue which was dissolved in chloroform (400 ml), treated with water (500 ml), and the mixture basified to pH 11 with 28% aqueous ammonia. The layers were shaken vigorously, separated, and the aqueous phase extracted with chloroform (2×200 ml). The combined chloroform extracts were washed with water, dried over $MgSO_4$, and evaporated to a white solid (10.9 g). The solid was dissolved in 95% ethanol (300 ml), and the stirred solution heated to reflux and then treated with a solution of (+)-dibenzoyl-D-tartaric acid (7.16 g, 0.02 m) in hot 95% ethanol (100 ml). A white solid crystallized immediately. The suspension was stirred and heated to reflux for 5 minutes, then allowed to cool. The white solid was collected by filtration and vacuum dried to give 17.0 g of (+)-cis-1,3,4,6,7,11b-hexahydro-2-methyl-7-pheny-2H-pyrazino[2,1-a]isoquinoline . (+)-dibenzoyl-D-tartrate (2:1), m.p. 205°–206°, $[\alpha]^{20} = +136.5°$ (C=0.2, $CH_3OH$).

(+)-Cis-1,3,4,6,7,11b-Hexahydro-2-methyl-7-phenyl-2H-pyrazino[2,1-a]isoquinoline dihydrochloride (+)-Cis-1,3,4,6,7,11b-Hexahydro-2-methyl-7-phenyl-2H-pyrazino[2,1-a]isoquinoline. (+)-dibenzoyl-D-tartrate (2:1) (16.9 g, 0.01886 m) was dissolved in chloroform (300 ml) and treated with water (600 ml), then basified to pH 11 with 28% aqueous ammonia. The layers were shaken vigorously and separated, and the aqueous phase extracted with chloroform (2×250 ml). The combined chloroform extracts were washed with water (2×100 ml) and dried over $MgSO_4$. Evaporation of the solvent gave 10.2 g of the white solid base. This was dissolved in methanol (200 ml), hot filtered, and the filtrate acidified with HCl gas. The white solid salt crystallized rapdily. The mixture was stirred and heated to reflux for 10 minutes, then allowed to cool. The solid was collected by filtration, washed with methanol, and vacuum dried at 85° for 24 hours to give 10.8 g of (+)-cis-1,3,4,6,7,11b-hexahydro-2-methyl-7-phenyl-2H-pyrazino[2,1-a]isoquinoline dihydrochloride, m.p. 274°–276° dec, $[\alpha]^{20} = +81.2°$ (C=1, 95% ethanol).

Specific aromatic substituted derivatives of the compound of formula I can be produced by aromatic substitution reactions, particularly aromatic nitration. These nitration reactions can be controlled to provide either specific nitration of the 7-phenyl ring (Example 13) or nitration of both the 7-phenyl and isoquinoline rings (Example 12). Such nitrated derivatives can be further elaborated by known methods to a wide variety of substituted derivatives. Thus the nitro derivative of Example 13 is readily reduced catalytically to the corresponding amine (Example 14). The amino function is selectively diazotized by treatment with sodium nitrite in acidic media, and the resulting diazonium salt can be subjected to Sandmeyer type halogenations (Example 15) or to thermal decomposition to give the phenolic derivative (Example 16). Treatment of the phenolic derivative with diazomethane gives the alkylated methoxy compound (Example 17).

EXAMPLE 12

Synthesis of cis-1,3,4,6,7,11b-Hexahydro-2-methyl-10-nitro-7-[4-nitrophenyl]-2H-pyrazino[2,1-a]isoquinoline dihydrochloride To a stirred solution of cis-1,3,4,6,7,11b-hexahydro-2-methyl-7-phenyl-2H-pyrazino[2,1-a]isoquinoline dihydrochloride (5.2 g, 0.015 m) in 98% sulfuric acid (30ml) maintained under nitrogen and cooled to ca $-5°$ in an ice-salt bath was added dropwise a solution of 90% nitric acid (5 ml) in 98% $H_2SO_4$ (20 ml) over a period of 30 minutes. The mixture was stirred for 30 minutes, then poured onto ice (250 ml) and the resulting solution extracted with chloroform (3×150 ml). The extracts were dried over $MgSO_4$ and evaporated to an off-white solid residue, 4.4 g. This residue was dissolved in a mixture of water (200 ml) and chloroform (200 ml), basified to pH 11 with 50% NaOH, and extracted with chloroform. The dried extracts were evaporated to a solid residue which was dissolved in methanol (50 ml) and acidified with HCl gas to give, after filtration, 3.66 g of salt. Recrystallization from methanol/water/ether and vacuum drying at 100° for 40 hours gave 1.36 g of cis-1,3,4,6,7,11b-hexahydro-2-methyl-10-nitro-7-(4-nitrophenyl)-2H-pyrazino[2,1-a]isoquinoline dihydrochloride, m.p. 244°–245°.

EXAMPLE 13

Synthesis of cis-1,3,4,6,7,11b-Hexahydro-2-methyl-7-(4-nitrophenyl)-2H-pyrazino[2,1-a]isoquinoline dihydrochloride To a stirred solution of cis-1,3,4,6,7,11b-hexahydro-2-methyl-7-phenyl-2H-pyrazino[2,1-a]isoquinoline dihydrochloride (10.0 g, 0.0285 m) in trifluoroacetic acid (100 ml) maintained at 0° under nitrogen was added dropwise over a period of 30 minutes 90% nitric acid (25 ml). The mixture was stirred for 2 hours, then poured onto ice (1000 ml). Chloroform (200 ml) was added and the mixture basified to pH 11 with 50% NaOH. The layers were separated and the aqueous phase extracted with chloroform (2×200 ml). The combined chloroform extracts were washed with water (500 ml), dried over $MgSO_4$, and evaporated to a yellow oil, 9.8 g. This was dissolved in methanol (200 ml), filtered, and the filtrate acidified with HCl gas. A white solid crystallized upon standing which was collected by filtration. This solid was recrystallized twice from methanol (200 ml) and water (10 ml) and vacuum dried at 95° for 24 hours to give 4.04 g of cis-1,3,4,6,7,11b-hexahydro-2-methyl-7-(4-nitrophenyl)-2H-pyrazino[2,1-a]isoquinoline dihydrochloride, m.p. 251°–252°.

EXAMPLE 14

Synthesis of cis-1,3,4,6,7,11b-Hexahydro-2-methyl-7-(4-aminophenyl)-2H-pyrazino[2,1-a]isoquinoline dihydrochloride A solution of cis-1,3,4,6,7,11b-hexahydro-2-methyl-7-(4-nitrophenyl)-2H-pyrazino[2,1-a)isoquinoline (5.2 g, 0.014 m) in methanol (500 ml), water (100 ml) and conc HCl (5 ml) was hydrogenated on a Parr apparatus over 2.0 g of palladium on carbon catalyst of 40 psi for 1 hour. The catalyst was removed by filtration and the solvents evaporated to a solid residue. This was dissolved in water (500 ml), basified to pH 11 with 50% NaOH, and extracted with ether (3×200 ml). The extracts were dried over $MgSO_4$ and evaporated to an oil, 4.04 g. This crude product was purified by chromatography on silica gel with a Prep 500 HPLC, eluting with 2% ammoniated methanol/chloroform. Pure fractions were combined and evaporated to give an oil, 1.12 g. This was dissolved in methanol (30 ml) and acidified with HCl gas. Upon standing, a white solid crystallized, which was collected by filtration and vacuum dried at 95% for 24 hours to give 1.08 g of cis-1,3,4,6,7,11b-hexahydro-2-methyl-7-(4-aminophenyl)-2H-pyrazino[2,1-a]isoquinoline dihydrochloride, m.p. 274°–276°.

EXAMPLE 15

Synthesis of cis-1,3,4,6,7,11b-Hexahydro-2-methyl-7-(4-chlorophenyl)-2H-pyrazino[2,1-a]isoquinoline dihydrochloride To a stirred solution of cis-1,3,4,6,7,11b-hexahydro-2-methyl-7-(4-aminophenyl)-2H-pyrazino[2,1-a]isoquinoline (6.0 g, 0.0205 m) in conc HCl (40 ml) maintained under nitrogen at 0° was added dropwise a solution of sodium nitrate (1.55 g, 0.0225 m) in water (10 ml) over a period of 30 minutes. The mixture was stirred an additional 15 minutes, then added dropwise to a solution of cuprous chloride (4.0 g, 0.04 m) in conc HCl (20 ml) maintained at 0°. After the addition was complete, the ice bath was removed and the mixture allowed to warm to ambient temperature and stirred for 3 hours, during which time nitrogen evolution was observed. The mixture was heated briefly to 60° for 3 minutes, then cooled and poured onto 1000 cc of ice/water, and treated with chloroform (300 ml), then basified to pH 11 with 50% NaOH. The mixture was stirred for 15 minutes, then a jelly-like precipitate removed by filtration through glass wool. The filtrate was transferred to a separatory funnel and the layers separated, the aqueous phase extracted with chloroform (2×100 ml), and the combined chloroform extracts dried and evaporated to a yellow oil, 5.84 g. This material was purified by chromatography on a Prep 500 HPLC on silica gel, eluting with 1.5% ammoniated methanol/chloroform. The pure fractions were combined and evaporated to an oil, 2.82 g. This was dissolved in methanol (30 ml) and acidified with HCl gas. Upon standing, a solid crystallized and was collected by filtration and vacuum dried at 90° for 24 hours to give 2.31 g of cis-1,3,4,6,7,11b-hexahydro-2-methyl-7-(4-chlorophenyl)-2H-pyrazino[2,1-a]isoquinoline dihydrochloride, m.p. 274°–276°.

EXAMPLE 16

Synthesis of cis-1,3,4,6,7,11b-Hexahydro-2-methyl-7-(4-hydroxyphenyl)-2H-pyrazino[2,1-a]isoquinoline dihydrochloride To a stirred solution of cis-1,3,4,6,7,11b-hexahydro-2-methyl-7-(4-aminophenyl)-2H-pyrazino[2,1-a]isoquinoline (6.14 g, 0.0209 m) in a mixture of water (100 ml) and 98% sulfuric acid (100 ml) maintained under nitrogen at 0° was added dropwise a solution of sodium nitrite (1.446 g, 0.0217 m) in water (20 ml). The mixture was stirred at 0° for 30 minutes, 20° for 30 minutes, and then heated to 80°–90° for 1 hour, after which time all nitrogen evolution had ceased. The mixture was cooled and poured onto 1000 cc of ice, then basified carefully to pH 7 with NaOH and extracted with chloroform (3×300 ml). The extracts were dried over MgSO4 containing decolorizing carbon, filtered and evaporated to give a pale yellow solid residue, 5.20 g. This was purified by chromatography on a Prep 500 HPLC on silica gel, eluting with 1.5% ammoniated methanol/chloroform. The pure fractions were combined and evaporated to give 2.14 g of a white solid. This was dissolved in methanol (150 ml) and acidified with HCl gas. A white solid crystallized which was collected by filtration and vaccuum dried to give 2.2 g of cis-1,3,4,6,7,11b-hexahydro-2-methyl-7-(4-hydroxyphenyl)-2H-pyrazino-[2,1-a]isoquinoline dihydrochloride, m.p. 284°-288°.

EXAMPLE 17

Synthesis of cis-1,3,4,6,7,11b-Hexahydro-2-methyl-7-(4-methoxyphenyl)-2H-pyrazino[2,1-a]isoquinoline dihydrochloride A solution of cis-1,3,4,6,7,11b-hexahydro-2-methyl-7-(4-hydroxyphenyl)-2H-pyrazino[2,1-a]isoquinoline (2.0 g, 0.0068 m) in methanol (200 ml) maintained at 5° was treated with a solution of diazomethane in ether (100 ml), prepared by treating N-nitrosomethylurea (10.0 g) with 40% potassium hydroxide (30 ml) at 0° and extracting the resulting diazomethane into ether. The mixture was allowed to warm to ambient temperature and hand-swirled occasionally for 6 hours. Acetic acid (5 drops) was added to decompose any remaining diazomethane, and the solvent was evaporated to an oily residue. This was treated with ether (200 ml) and 5% NaOH (200 ml), agitated until all the residue was dissolved, and the layers separated. The aqueous phase was extracted with ether (2×100 ml) and the combined ether extracts washed with 5% NaOH (3×100 ml) and dried over MgSO4. Evaporation of the solvent gave an oily residue, 1.9 g, which was dissolved in methanol (30 ml), filtered, and acidified with HCl gas. Upon standing, an off-white solid crystallized which was collected by filtration, washed with methanol/ether and vacuum dried at 95% for 24 hours to give 2.03 % of cis-1,3,4,6,7,11b-hexahydro-2-methyl-7-(4-methoxyphenyl)-2H-pyrazino[2,1-a]isoquinoline dihydrochloride, m.p. 272°-274° dec.

The compound of formula I may be used in the form of pharmaceutical preparations which contain it in association with a compatible pharmaceutical carrier. The pharmaceutical preparations may be made up for enteral, (for example, oral) or parenteral administration. The dosage form may be a solution, suspension, tablet, capsule, powder or granule product or other suitable formulation.

It will be apparent to those skilled in this art that many modifications and changes may be made in the invention described above without departing from the scope and spirit of the invention.

What is claimed is:

1. The compound

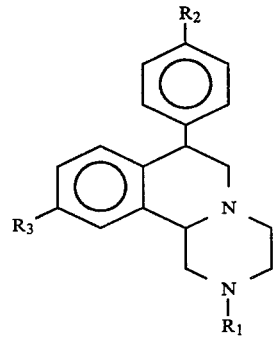

wherein $R_1$ is hydrogen, $C_1$–$C_7$ alkyl, $C_3$–$C_7$ cycloalkyl, $C_1$–$C_7$ alkanoyl, $C_7$–$C_8$ phenylalkyl, phenylacetyl, phenyl or benzoyl, and $R_2$ and $R_3$ are the same or independently hydrogen, halogen, hydroxy, $C_1$–$C_7$ alkanoyloxy, nitro, amino $C_1$–$C_7$ aminoalkyl, trifluoromethyl, $C_1$–$C_7$ alkyl, $C_1$–$C_7$ alkoxy, $C_1$–$C_7$ alkanoyl, cyano, $C_1$–$C_7$ alkylamino and acid addition salts thereof.

2. The compound of claim 1 wherein $R_1$, $R_2$ and $R_3$ are hydrogen.

3. The cis form of the compound of claim 2.

4. The acid addition salt of the compound of claim 3.

5. The compound of claim 1 wherein $R_1$ is $C_1$–$C_7$ alkyl.

6. The cis form of the compound of claim 5.

7. The compound of claim 5 wherein $R_1$ is methyl and $R_2$ and $R_3$ are hydrogen.

8. The cis form of the compound of claim 7.

9. The acid addition salt of the compound of claim 8.

10. The (+) optical isomer of the compound of claim 9.

11. The (−) optical isomer of the compound of claim 9.

12. The trans form of the compound of claim 7.

13. The acid addition salt of the compound of claim 12.

14. The compound of claim 5 wherein $R_1$ is $C_1$–$C_7$ alkyl and $R_2$ and $R_3$ are members of the class of hydrogen, $C_1$–$C_7$ alkyl, halogen, $C_1$–$C_7$ alkoxy, hydroxy, nitro and amino.

15. The compound of claim 14 wherein $R_1$ is methyl and $R_3$ is hydrogen.

16. The compound of claim 1 wherein $R_1$ is $C_7$–$C_8$ phenylalkyl and $R_2$ and $R_3$ are hydrogen.

17. The compound of claim 1 wherein $R_1$ is benzoyl or phenylacetyl and $R_2$ and $R_3$ are hydrogen.

18. A process for relieving depression in warm-blooded animals requiring such relief which comprises providing to said animals an effective dosage of the compound of claim 1 in association with a compatible pharmaceutical carrier.

* * * * *